United States Patent [19]

Gaudette et al.

[11] 4,058,528
[45] Nov. 15, 1977

[54] 5-HYDROXYHEXAHYDROPYRIMIDINE

[75] Inventors: Roger Robert Gaudette, Hudson, N.H.; John Leonard Ohlson, Bedford; Patricia Marie Scanlon, Arlington, both of Mass.

[73] Assignee: W. R. Grace & Co., New York, N.Y.

[21] Appl. No.: 703,184

[22] Filed: July 7, 1976

Related U.S. Application Data

[62] Division of Ser. No. 630,791, Nov. 11, 1975, Pat. No. 3,988,367.

[51] Int. Cl.$^2$ ............................................. C07D 239/04
[52] U.S. Cl. ................................................. 260/251 R
[58] Field of Search ..................................... 260/251 R

[56] References Cited

U.S. PATENT DOCUMENTS 3,658,817  4/1972  Orlando ........................... 260/251 R

OTHER PUBLICATIONS

Chem. Abst., vol. 66, (1967), p. 28727d.
Chem. Abst., vol. 66, (1967), p. 28731a.
Chem. Abst., vol. 32, p. 469h.
Chem. Abst., vol. 50, p. 1780h.
J. Am. Chem. Soc., (1946), vol. 68, pp. 1611–1613.

Primary Examiner—Delbert R. Phillips
Attorney, Agent, or Firm—Elton Fisher

[57] ABSTRACT

N,N'-Dicarboxymethyl-1,3-propanediamine (designated PDDA) is prepared by reacting 1,3-propanediamine with formaldehyde and HCN to form hexahydropyrimidine-1,3-diacetonitrile, which is hydrolyzed with an aqueous alkali metal hydroxide to form dialkali metal hexahydropyrimidine-1,3-diacetate which, in turn, is reacted with mineral acid to form the desired PDDA and formaldehyde.

N,N'-Dicarboxymethyl-2-hydroxy-1,3-propanediamine (designated HYDROXY-PDDA) is prepared by reacting 1,3-diamino-2-propanol with formaldehyde and HCN to form 5-hydroxyhexahydropyrimidine-1,3-diacetonitrile, which is hydrolyzed with an aqueous alkali metal hydroxide to form dialkali metal 5-hydroxyhexahydropyrimidine-1,3-diacetate which, in turn, is reacted with acid to form the desired HYDROXY-PDDA and formaldehyde.

1 Claim, No Drawings

5-HYDROXYHEXAHYDROPYRIMIDINE

CROSS-REFERENCE TO RELATED APPLICATIONS

This is a divisional of application Ser. No. 630,791, filed Nov. 11 1975, now U.S. Pat. No. 3,988,367.

BACKGROUND OF THE INVENTION

This invention is in the field of; (a) N,N'-dicarboxymethyl -1,3-propanediamine, which has the formula

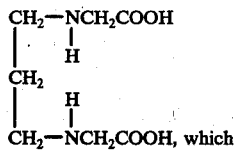

is sometimes called 1,3-propanediamino-N,N'-diacetic acid and which is designated PDDA; and (b) N,N'-dicarboxymethyl-2-hydroxy-1,3-propanediamine which has the formula

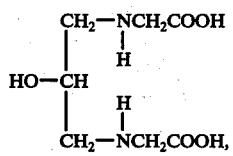

which is sometimes called 2-hydroxy-1,3-propanediamine-N,N'-diacetic acid and which is designated HYDROXY-PDDA.

More particularly, this invention is directed to an improved process for preparing PDDA of high quality by an improved route involving the following sequential reactions:

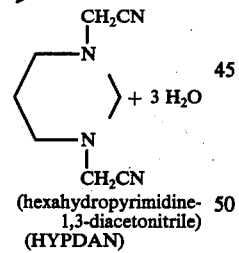
(hexahydropyrimidine-1,3-diacetonitrile) (HYPDAN)

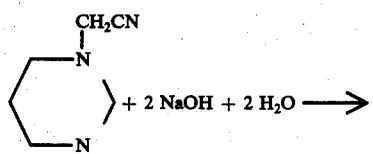

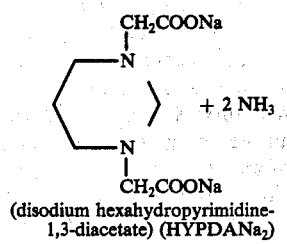
(disodium hexahydropyrimidine-1,3-diacetate) (HYPDANa$_2$)

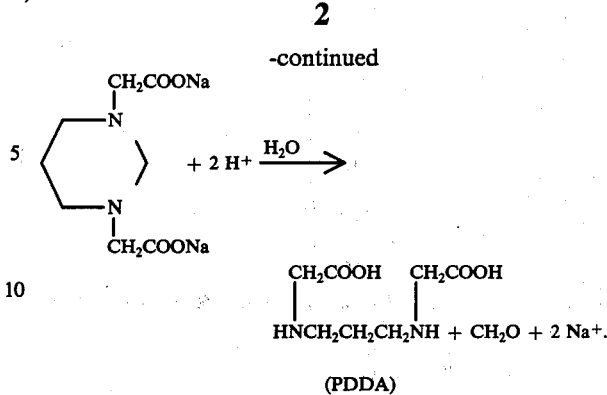
(PDDA)

This invention is also directed to HYDROXY-PDDA and to a process for preparing HYDROXY-PDDA of high quality by the following sequential reactions:

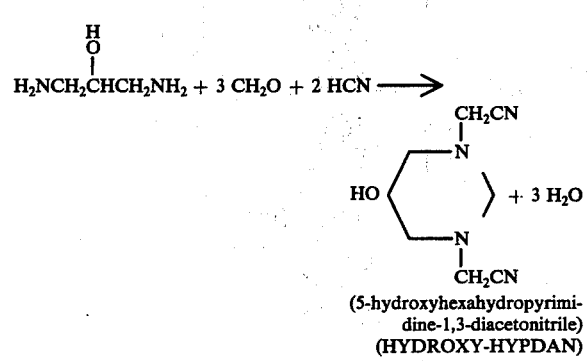
(5-hydroxyhexahydropyrimidine-1,3-diacetonitrile) (HYDROXY-HYPDAN)

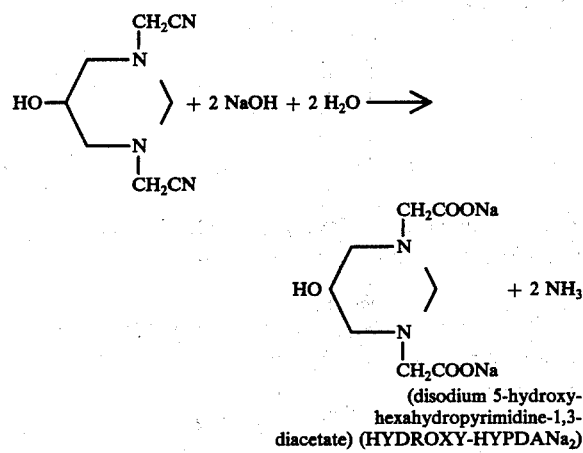
(disodium 5-hydroxyhexahydropyrimidine-1,3-diacetate) (HYDROXY-HYPDANa$_2$)

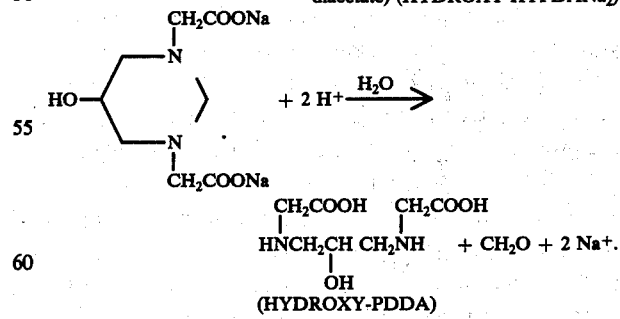
(HYDROXY-PDDA)

Prior art methods of preparing PDDA are taught by Johnson et al., J. Org. Chem. 1962, 27, 2077-2080. See the second column on page 2079 and the first column on page 2080.

The preparation of

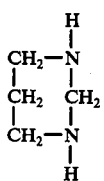

is taught by Titherly et al, J. Chem. Soc., 1913, 103, 330–340 (at 334).

The preparation of

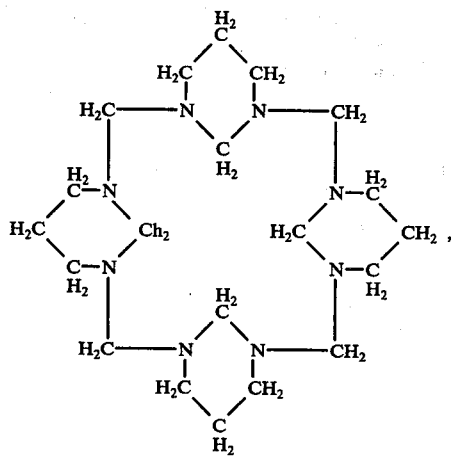

which, elsewhere in this specification, is referred to as

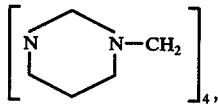

from formaldehyde and 1,3-propanediamine is taught by Krässig, Makromol. Chem., 1956, 17, 77–130 (at 87–88).

The process of the instant invention constitutes a decided improvement over prior art routes to PDDA. Among the advantages of the process of the instant invention are; (a) the fact that PDDA formed by the method of this invention is free of side products; (b) the by-products (NH₃, formaldehyde, and an alkali metal salt, e.g., sodium or potassium chloride or sulfate) are readily separated from the respective intermediate or final product with which the by-product is formed; (c) the use of objectional or inconvenient materials such as anhydrous HCl and hydrogenation catalysts is avoided; and (d) the final product is substantially pure PDDA which is obtained without resorting to the expensive and inconvenient repeated decantations and crystallizations of the prior art.

SUMMARY OF THE INVENTION

In summary this invention is directed to a nitrile having the formula

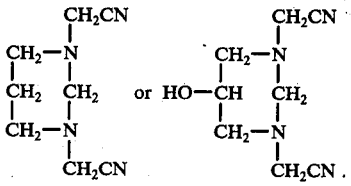

DESCRIPTION OF PREFERRED EMBODIMENTS

In one preferred embodiment ("Embodiment A") this invention is directed to a process for preparing the nitrile of the above Summary, said process comprising admixing in an aqueous medium: (a) 1,3-propanediamine or 1,3-diamino-2-propanol; and (b) formaldehyde and HCN or formaldehyde and glycolonitrile in amounts effective for forming said nitrile.

Preferred mole ratios of amine to formaldehyde to HCN are 1:3–3.5:2–2.5 or 1:3–3.1:2:2.1, preferred mole ratios of glycolonitrile to formaldehyde are 2:1 or 2:0.9–1.1, and preferred mole ratios of HCN or glycolonitrile to 1,3-propanediamine or 1,3-diamino-2-propanol are 2:1 or 2:0.9–1.1.

It is generally preferred that the mixture formed by admixing the amine, formaldehyde, and HCN or glycolonitrile be prepared at 45°–70° C ( or 50°–60° C) and maintained at said temperature to form the nitrile. However, excellent results have been obtained where said mixture was prepared at 20°–80° C and maintained at 40-60° C to form the nitrile. It is generally preferred to maintain said mixture at 50°–60° C (or 55°–60° C) for 1–5 hours (or 2–4 hours) to form the nitrile.

In another preferred embodiment ("Embodiment B") this invention is directed to a salt having the formula

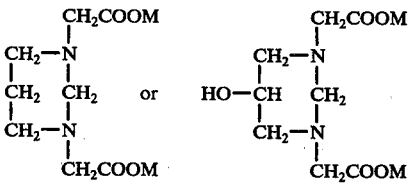

in which M is an alkali metal cation (e.g., sodium or potassium) or ½ of an alkaline earth metal cation (i.e., barium, strontium, or calcium), or an ammonium ion having the formula

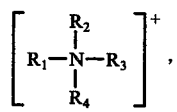

where $R_1$, $R_2$, $R_3$, and $R_4$ is each independently selected from a group consisting of hydrogen, lower alkyl, or hydroxy lower alkyl.

In another embodiment ("Embodiment C") this invention is directed to a process for preparing the alkali metal and alkaline earth metal salts of Embodiment B, said process comprising hydrolyzing the nitrile of the above Summary in an aqueous medium with an amount of an alkali metal hydroxide (e.g., sodium or potassium hydroxide) or an alkaline earth metal hydroxide effective for hydrolyzing the nitrile. Generally a mole ratio of nitrile to alkali metal hydroxide of 1:2.2–2.4 or 1:2.02-2.20 is preferred (where using an alkaline earth metal hydroxide the mole ratio of nitrile to alkaline earth metal hydroxide would be 1:1.1-1.2 or 1:1.01-1.1). The hydrolysis has been conducted with excellent results at about 95°-110° C. Where using temperatures above the normal boiling point of the reaction mixture in which the hydrolysis occurs, an apparatus designed to conduct the hydrolysis under superatmospheric pressure can be used. However, this is not necessary because excellent results have been obtained where conducting the hydrolysis at the normal boiling point of the mixture in which the nitrile is being hydrolyzed. Residence time in the hydrolysis zone has been varied from 1-3 hours with excellent results, but a residence time of 1.5-2 hours is generally preferred. It is preferred to boil the mixture in which the hydrolysis occurs until said mixture is free of by-product ammonia.

In another preferred embodiment ("Embodiment D") this invention is directed to a process for forming an acid selected from a first group consisting of

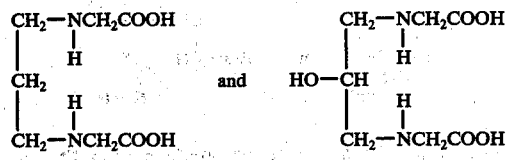

comprising:

a. forming a nitrile selected from a second group consisting of

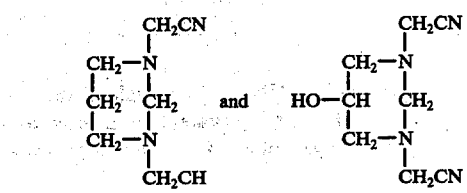

by admixing, in an aqueous medium formaldehyde; (i) a member selected from a third group consisting of HCN and glycolonitrile; and (ii) a member selected from a fourth group consisting of 1,3-propanediamine and 1,3-diamino-2-propanol, to form a resulting admixture and maintaining the resulting admixture at a temperature effective for forming the second group member for a time effective for forming the second group member, the formaldehyde, the third group member, and the fourth group member being admixed in amounts effective for forming the second group member;

b. hydrolyzing said nitrile in an aqueous medium with an amount of an alkali metal hydroxide or alkaline earth metal hydroxide effective for hydrolyzing the nitrile to form a salt selected from a fifth group consisting of

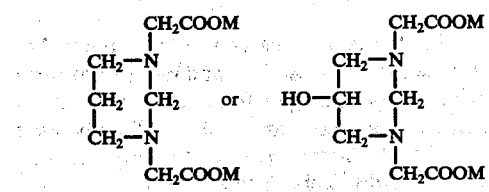

in which M is an alkali metal ion or ½ of an alkaline earth metal cation (e.g., ½ Ba++, ½ Sr++, or ½ Ca++); and c. converting said salt to the acid having a formula

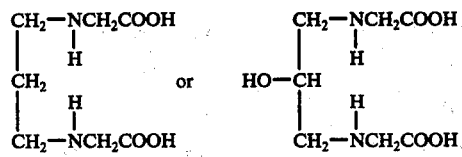

by treating said salt in an aqueous medium with an amount of a mineral acid or an acidic ion exchange resin effective for forming said first group member.

The mixture formed by admixing formaldehyde, HCN, and the fourth group member (or formaldehyde, glycolonitrile and fourth group member) is preferably prepared at 45°-70° C (or 50°-60° C) and maintained at said temperature (or at 55°-60° C) for 1-5 hours (or 2-4 hours) to form the second group member.

Sodium hydroxide is a preferred alkali metal hydroxide for use in the process of this embodiment. An alkaline earth metal hydroxide (e.g., Ba(OH)₂, Sr(OH)₂, or Ca(OH)₂) can be used in place of the alkali metal hydroxide. Obviously, where using an alkaline earth metal hydroxide, ½ mole is equivalent to 1 mole of an alkali metal hydroxide.

The hydrolysis of the nitrile is generally conducted at about the normal boiling point of the aqueous medium in which the hydrolysis is conducted. However, lower temperatures (e.g., 90°-100° C) have given excellent results, and excellent results can be obtained at higher temperatures (e.g., 110°-120° C) where using a pressurized system. It is generally preferred to boil the aqueous medium in which the hydrolysis of the nitrile is being (or has been) conducted until said medium is substantially free of by-product ammonia.

In general it is preferred to use 2.0-2.5 (2.0-2.05) moles of a monoprotic acid or 1-1.25 (or 1-1.02) moles of a diprotic acid per mole of the fifth group member to convert said fifth group member (the aforesaid salt) to the first group member. Hydrochloric acid is a preferred mineral acid. Where using an acidic ion exchange resin to convert the fifth group member (the salt) to the first group member, it is generally preferred to use 2-3 (or 2.2-2.6) equivalents of an acidic ion exchange resin per mole of the fifth group member.

Where treating the fifth group member (the aforesaid salt) in an aqueous medium with hydrochloric acid to form the first group member (the acid of this invention), it is often advantageous to use an excess of hydrochloric acid (preferably added as concentrated e.g., 33-40% HCl aqueous hydrochloric acid solution) to precipitate the product acid (first group member) as a dihydrochloride salt having the formula

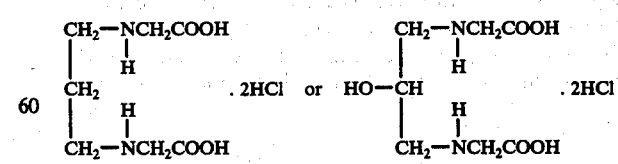

In other words, the salt (the fifth group member) which is present as an aqueous solution is treated with an amount of hydrochloric acid effective for forming and precipitating a sixth group member (a hydrochloride having the formula

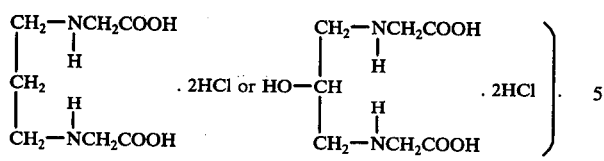

Excellent results have been obtained where providing 4–8 (or 4–6) moles of hydrochloric acid per mole of fifth group member (the aforesaid salt).

The above-mentioned sixth group member (said hydrochloride) can be converted to the first group member (an acid having the formula

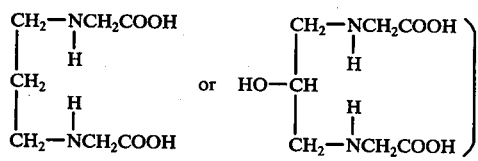

by treating the sixth group member (preferably in an aqueous medium) with a stoichiometric amount of sodium (or potassium) hydrogen carbonate. For this purpose a stoichometric amount of the sodium (or potassium) hydrogen carbonate is two moles per mole of the sixth group member. Ammonium carbonate, ammonium hydrogen carbonate, or ammonium carbamate can also be used to convert the hydrochloride to the free acid.

Alternatively, the first group member (the acid having the formula

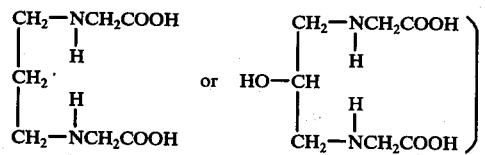

can be precipitated from the aqueous medium in which it (the first group member) was formed by adding to said aqueous medium an amount of a water soluble alcohol (e.g., methyl alcohol, ethyl alcohol, or iso-propyl alcohol) effective for precipitating the first group member. Excellent results were obtained where adding such amount of the alcohol that the alcohol constituted about 75–95% (or 90–95%) of the aqueous medium after the first group member had been precipitated therefrom.

The first group member of Embodiment D can be converted to the sixth group member — the above described hydrochloride — by treating the first group member with hydrochloric acid (e.g., 4–8 or 4–6 moles of hydrochloric acid per mole of first group member.

In another preferred embodiment ("Embodiment E") this invention is directed to an acid having the formula

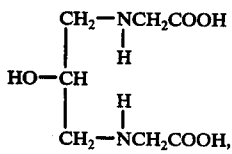

and to a hydrochloride of said acid, the hydrochloride having the formula

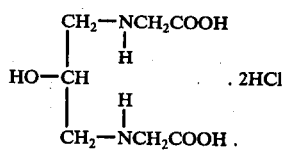

In another preferred embodiment of this invention ("Embodiment F"), which is equivalent to the embodiment recited in the above Embodiment A, the procedure of step "(a)" of Embodiment D, supra, was modified by:

1. Admixing in an aqueous medium 1,3-propanediamine or 1,3-diamio-2-propanol and formaldehyde, the amine and the formaldehyde being admixed in an amount effective for forming a compound having the formula

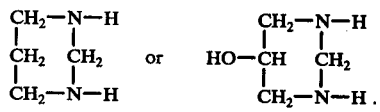

2. Admixing in an aqueous medium; (a) the compound having the formula

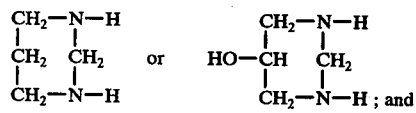

b. formaldehyde plus HCN the equivalent thereof (e.g., glycolonitrile which is equivalent on a mole-for-mole basis to formaldehyde plus HCN), said compound having the formula

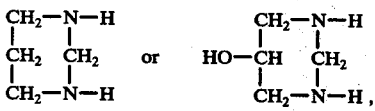

said formaldehyde, and said HCN being admixed in amounts effective for forming a nitrile having the formula

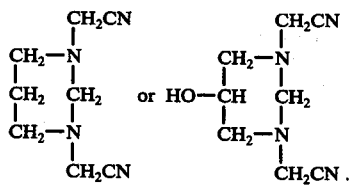

3. Substituting the thus prepared nitrile in step "b" of the procedure set forth in said Embodiment D to form the salt (fifth group member) formed in step "b" of Embodiment D. The thus formed salt can then be used in step "c" of said Embodiment D to form the first group member of said Embodiment D.

We have obtained excellent results with this procedure (the procedure of Embodiment F) by admixing the amine and formaldehyde in a mole ratio of 1:1–1.5 (or 1:1.0–1.05) and maintaining the resulting mixture at about 50°-70° C (or 55°-65° C) for about 0.25-16 hours (or 0.5-1 hour).

We have also obtained excellent results with this procedure (that of Embodiment F) by admixing the compound having the formula

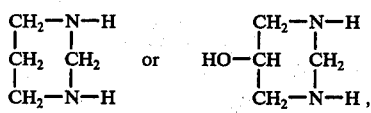

the formaldehyde and the HCN in a mole ratio of 1:2.0–2.5: 2.0–2.5 (or 1:2.0–2.1:2.0–2.1) at about 45°-70° C (or 50°-60° C) and maintaining the resulting mixture at 40°-60° C) (or 55°-60° C) for about 1-5 hours (or 2-4 hours) to form the aforesaid nitrile. Alternatively, the formaldehyde and HCN can be replaced with a glycolonitrile which is equivalent to formaldehyde plus HCN.

In another preferred embodiment ("Embodiment G") this invention is directed to a process for forming a nitrile having the formula

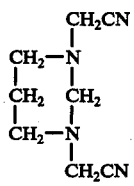

comprising mixing: (a) a tetramer of 1,3-propanediamine and formaldehyde; (b) formaldehyde; and (c) HCN and maintaining the resulting mixture at a temperature effective for forming said nitrile for a time effective for forming said nitrile, the tetramer, formaldehyde, and HCN being admixed in amounts effective for forming said nitrile.

Preferred mole ratios of the tetramer to formaldehyde to HCN are 1:3.2–4.8:7.2–8.8. Glycolonitrile, (one mole or which is equivalent to one mole of formaldehyde plus one mole of HCN) can be substituted on a mole-for-mole basis for HCN plus formaldehyde. A preferred reaction temperature is about 45°-70° C and a preferred residence (reaction) time is about 20-90 minutes (or 25-40 minutes).

A nitrile having the formula

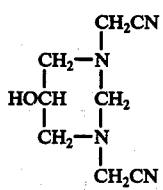

can be formed by substituting a tetramer or 1,3-diamino-2-propanol for the tetramer of 1,3-propanediamine in Embodiment G. (See Procedure 17.)

In another preferred embodiment ("Embodiment H") a product salt having the formula

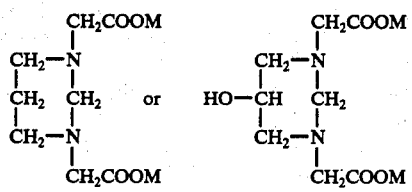

in which M is an alkali metal cation, ½ of an alkaline earth metal cation, or an ammonium ion having the formula

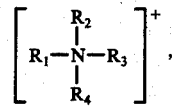

in which each of $R_1$, $R_2$, $R_3$, and $R_4$ is selected from a group consisting of hydrogen, lower alkyl, or hydroxy lower alkyl can be prepared by admixing in an aqueous medium a reactant salt having the formula

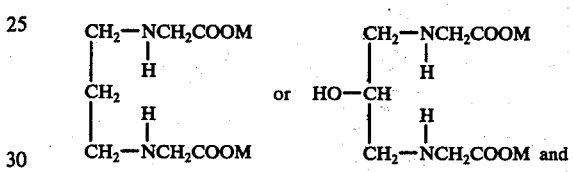

an amount of formaldehyde effective for forming the product salt.

DETAILED DESCRIPTION OF THE INVENTION

This invention is directed to the preparation of: (a) PDDA; and (b) intermediates on a route to PDDA from 1,3-diaminopropane, formaldehyde and HCN, and to said intermediates.

This invention is also directed to HYDROXY-PDDA, to intermediates on a route to HYDROXY-PDDA from 1,3-diamino-2-propanol, formaldehyde and HCN, to the preparation of HYDROXY-PDDA, and to the preparation of said intermediates.

PDDA and HYDROXY-PDDA are useful for forming chelates of copper. Such copper chelates are useful to control the concentration of copper ions in metal plating baths and as a means for supplying copper to soil which is deficient in copper.

PDDA and HYDROXY-PDDA are also useful for preparing chelating compounds having the formula

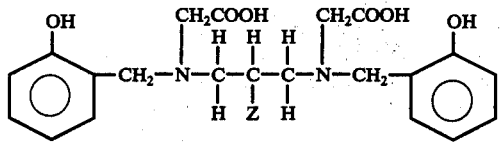

in which Z is H or OH.

Chelating compounds having the above formula are especially useful for chelating iron (iron(III) and iron (II). These chelating agents, their preparation, the preparation and use of such iron chelates is taught in our copending U.S. patent application Ser. No. 630,792, filed Nov. 11, 1975 which is assigned to W. R. Grace & Co. now U.S. Pat. No. 3,988,367.

The instant invention will be better understood by referring to the following specific but nonlimiting examples and procedures. It is understood that said invention is not limited by said examples or by said procedures all of which are offered merely as illustrations; it is also understood that modifications can be made without departing from the spirit and scope of the invention.

The examples were actually run.

The procedures, while not actually run, will illustrate certain embodiments of out invention.

EXAMPLE 1

A 74.1g portion (1 mole) of 1,3-propanediamine was fed into 50 ml. of water in a reaction zone. 68.2g (1 mole) of 44% formaldehyde was fed into the aqueous amine solution in said reaction zone over a period of 40 minutes while maintaining the temperature of the resulting mixture at 50°-70° C. The thus formed mixture was cooled to 50° C in the reaction zone and 166.4g of 68.5% glycolonitrile was added thereto over a period of 50 minutes. The temperature of the mixture in the reaction during the first half of the glycolonitrile addition thereto; cooling was applied to the reaction zone followed by heating, said temperature being maintained at 45° to 55° C. The clear, colorless solution was stirred an additional 1¾ hours and allowed to stand overnight.

When the straw-colored solution was agitated on the next day a mass of white crystals formed. The mass was broken up, added to water, stirred, and filtered. After reslurrying twice in 500 ml portions of water, the collected product was dried at 45°-50° C. 63.6 g of product (nitrile) corresponding to a conversion (one pass yield) of 38.3% was obtained.

A small sample of the above prepared nitrile was taken for analysis. This aliquot was titrated with perchloric acid in glacial acetic acid. A monoperchlorate salt was formed during the titration. The results of this titration showed a molecular weight of 164 v. a theoretical value of 164. The product was identified by gas chromatography and infrared spectroscopy as substantially pure hexahydropyrimidine- 1,3-diacetonitrile (HYPDAN),

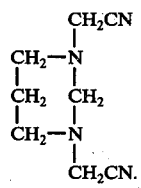

EXAMPLE 2

A 370.5g portion (5 moles) of 1,3-propanediamine was fed into 250 ml of water in a reaction zone. 341.0g of 44% formaldehyde was fed into the aqueous amine solution in said reaction zone over a period of 30 minutes while maintaining the temperature of the resulting mixture at 50°-63° C. The thus formed mixture was stirred an additional 40 minutes and allowed to stand overnight.

832.0g (10 moles) of 68.5% glycolonitrile was added thereto over 40 minutes. The temperature rose from 21° C to 54° C during the glycolonitrile addition. Half way through said addition, 275 ml of water was also fed into the reaction zone. The resultant mixture was stirred at 50°-57° C for two hours, during which time cyrstals formed. An additional 250 ml of water was added to the mixture halfway through said 2-hour period. The reaction mixture was cooled over three hours to 23° C, filtered, and the product crystals were washed with 125 ml of water. The product was dried in air to give 694g of HYPDAN, corresponding to a conversion of 85%.

EXAMPLE 3

A 74.1g portion (1 mole) of 1,3-propanediamine was fed into 50 ml of water in a reaction zone. The resulting aqueous solution of the amine which became hot ( reaching a temperature of about 60° C as it was formed), was cooled to 50° C, and 68.2g (1 mole) of 44% formaldehyde solution was fed into he aqueous amine solution in said reaction zone over a period of 45 minutes while maintaining the temperature of the resulting mixture at 50°-70° C. The thus formed mixture was cooled to 47° C in the reaction zone and a premix of 136.4g (2 moles) of 44% formaldehyde solution and 84 ml (2.1 moles) of HCN (which had been stabilized with 0.4g of 85% $H_3PO_4$) having a temperature of 15° C was added thereto over a period of 50 minutes. The temperature of the mixture in the reaction zone increased as the formaldehyde and HCN were added thereto; said temperature reached a maximum of 65° C. Within two minutes of the end of the premix feed, white cyrstals of the nitrile product precipitated. The mixture from which the crystals precipitated (with the crystals therein) was stirred two hours while maintaining it at 50°-55° C. The mixture was then cooled to 25° C, filtered, and the nitrile crystals were washed with cold water. The recovered nitrile was dried at 50° C. 138.5g of product (HYPDAN) corresponding to a conversion (one pass yield) of 85% was obtained.

EXAMPLE 4

A 148.2g portion (2 moles) of 1,3-propanediamine was fed into 100 ml of water in a reaction zone. The resulting aqueous solution of the amine which became hot (reaching a temperature of about 60° C as it was formed), was cooled to 23° C, and 136.4g (2 moles) of 44% formaldehyde solution was fed into the aqueous amine solution in said reaction zone over a period of 40 minutes. The temperature of the reaction mixture rose to a maximum of 69° C by the end of the formaldehyde feed. After stirring for 20 minutes, 275g (4 moles) of 44% formaldehyde and 168 ml (4.3 moles) of hydrogen cyanide were fed into the reaction zone simultaneously from separate reservoirs over a period of 65 minutes while maintaining the temperature of the resultant mixture at 52°-69° C. Cooling was required twice during this 65-minute feed period. The reaction mixture was stirred at 53°-69° C for two hours, although the reaction was essentially complete in 1½ hours when analyzed. Product crystallized from the reaction mixture upon seeding with a small amount of HYPDAN during the 2-hour hold period. The slurry was cooled to 20° C over 25 minutes and centrifuged and the collected product was washed with 65 ml of water from a spray nozzle. The product was allowed to dry. 277g (or 84% yield) of HYPDAN crystals was obtained.

EXAMPLE 5

A 246g portion (1.5 moles) of the nitrile prepared in Example 2 was hydrolyzed by saponification with 552g (3.2 moles) of 22.8% sodium hydroxide at about 100°-106° C. The resulting hydrolyzed mixture was boiled at atmospheric pressure until substantially all by-product ammonia had been vaporized therefrom to form an ammonia-free solution. This required about 1.25 hours. During the above mentioned hydrolysis and boiling periods water was added as necessary to maintain the volume of the system substantially constant. The final weight of the very light straw-colored sodium salt solution was 851g.

A small portion of the above prepared ammonia-free solution was taken for analysis leaving a major portion of said solution for further processing. An attempt was made to titrate a small portion of ammonia-free solution with copper (II) chloride at pH 9g but the product did not chelate copper (II). However, at pH 6.0, $CH_2O$ was released and the copper (II) ion was chelated. The sodium salt was disodium hexahydropyrimidine-1,3- diacetate ($HYPDANa_2$),

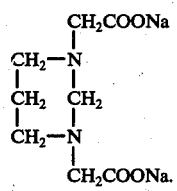

Titration of a weight portion of the ammonia-free sodium salt solution with copper (II) chloride at pH 6 using a copper (II) selective electrode established that conversion (one pass yield) of HYPDAN to HYPDANa$_2$ was 100% of theory based on the nitrile charged. A gas chromatogram of the acidified, dried, and silylated product (HYPDANa$_2$) showed that the HYPDANa$_2$ was substantially free of impurities.

EXAMPLE 6

The major portion of the HYPDANa$_2$ solution prepared in Example 5 was diluted to 2 liters with water; the resulting aqueous system was acidified by passing it through a tube containing about 2.6 equivalents (17% deficiency) of Amberlite 200 (a strongly acidic cation exchange resin). A 900 ml fraction of pH 2.8 to 4.1 product solution was collected from the bottom of the column. Said product solution smelled strongly of formaldehyde; such odor was not evident in the original sodium salt solution. The fraction was evaporated in air. When the fraction became syrupy, it was mixed with methanol. A solid product precipitated. The precipitate was filtered off, methanol washed, and dried at 50° C. An aqueous solution of the dried solid product chelated copper (II) at pH 9 (unlike the original sodium salt solution) and at pH 6. Acid-base titrations, copper (II) titrations, gas chromatograms, and an infrared spectogram showed the solid is 1,3-propane- diamine-N,N'-diacetic acid (PDDA),

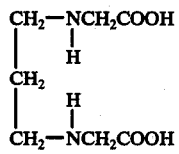

This yielded 106.8 g of PDDA, which is a 37.5% recovery. The remaining alkaline fractions were eluted with 1.5 liter of $H_2O$.

The above mentioned alkaline fractions were run through the same column after the resin was regenerated. A 700 ml fraction of pH 3.0 to 4.4 was collected and evaporated in air. PDDA was isolated by using the methanol precipitation procedure described supra. This pass yielded 74.5 g of PDDA, or a total of 63.6% recovery. A 1 liter fraction having a pH of 6 to 11 which was eluted with the aid of a dilute ammonia solution was also collected.

EXAMPLE 7

The resin in the column of Example 6 was replaced by Amberlite IRC 84 ( a weakly acidic ion exchange resin). The final 1l alkaline fraction obtained in EXAMPLE 6 was passed through the new resin. The Amberlite IRC 84 did not absorb the PDDA zwitterions as tenaciously as the Amberlite 200. PDDA was eluted with distilled water. An 850 ml fraction of pH 3.4 to 4.4 was collected and evaporated in air. PDDA was isolated as in EXAMPLE 6.

EXAMPLE 8

810 ml of concentrated hydrochloric acid (37.5% HCl) was added to 1,000 g of a 39.3% HYPDANa$_2$ solution with stirring. This resulted in the precipitation of white crystalline material which was identified as PDDA dihydrochloride,

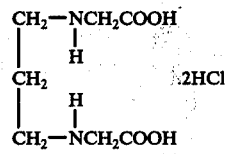

The PDDA dihydrochloride of Example 8 was dissolved in 600 ml water and treated with concentrated aqueous ammonia to pH 3.8. The resultant PDDA/ammonium chloride solution (1250 ml total) was mixed with 6l of methanol. White solids precipitated. The mixture was stirred overnight. The precipitate was filtered off and slurried with 4l of methanol for three hours. The crystalline product was filtered, washed with methanol, and dried in air. The yield was 203 grams of 92.4% PDDA, or a 62% recovery.

EXAMPLE 10

A 39.2g portion (0.2 mole) of 50% sulfuric acid followed by 5 ml of concentrated (95.7%) sulfuric acid was added to 62.6g (0.1 mole) of 39.3% HYPDANa$_2$. The resultant solution was allowed to stand for a few days to slowly evaporate. Crystals formed during this standing period. The crystalline product was filtered off, washed with a small amount of $H_2O$, and dried at 50° C. A 14.8g yield was obtained and was shown to be 97.3% PDDA sulfate, i.e., PDDA-H$_2$SO$_4$, having the formula

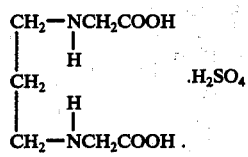

Recovery was 50% of theory

EXAMPLE 11

An 18.0g (0.2 mole) portion of 1,3-diamino-2-propanol was added to a reaction zone and diluted to about 40 ml with water. 13.8g (0.2 mole) of 44% formaldehyde solution was fed into the aqueous amine solution in said reaction zone over a period of four minutes at 30° to 70° C. The thus formed mixture was allowed to cool with stirring over 15 minutes to 47° C and was analyzed by gas chromatography. The gas chromatogram showed that the major component of the mixture was not 1,3-diamino-2-propanol but a formaldehyde adduct of it, namely, 5-hydroxyphexahydropyrimidine,

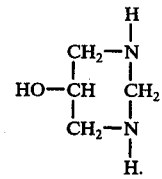

EXAMPLE 12

The thus analyzed reaction mixture of EXAMPLE 11 above was further reacted with 34.0g (0.41 mole) of 68.5% glycolonitrile, fed into the reaction zone over 6 minutes at 47° to 58° C. The resultant mixture was heated at 45° to 55° C for almost three hours and then cooled to 25° C. The final reaction mixture, a yellow solution, was analyzed by gas chromatography. The major component was found to be the product 5-hydroxyhexahydropyrimidine-1,3-diacetonitrile (HYPDANOL),

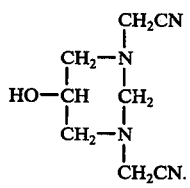

EXAMPLE 13 the HYPANDOL obtained in Example 12 was saponified in 34.4 g(0.43 mole) of 50% NaOH diluted with about 100 ml of water at 99°–105° C. The HYPDANOL solution was added portion-wise to the hot caustic solution over 15 minutes, and the resulting hydrolyzed mixture was boiled at atmospheric pressure until substantially all by-product ammonia had been vaporized (about 1.5 hours). Water was added during the boil-off period to maintain volume. The final weight of the yellow solution was 146.1 g.

A small portion of the above prepared ammonia-free solution was taken for analysis; the major portion of said solution left for further processing into a very stable, iron-specific chelating agent. An attempt was made to titrate a small portion of the ammonia-free solution with copper (II) chloride at pH 9. Like HYPDANa$_2$, this solution did not chelate copper (II). However, like HYPDANa$_2$, CH$_2$O was released at pH 6.0, and the solution chelated copper (II). The sodium salt was disodium 5-hydroxyhexahydropyrimidine- 1,3-diacetate (HYPDA-OLNa$_2$),

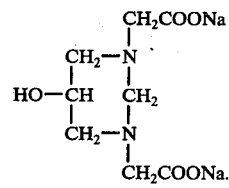

Titration of a weighed portion of this HYPDA-OLNa$_2$ with copper (II) chloride at pH 6 using a copper (II) selective electrode established that conversion (one pass yield) of 1,3-diamino-2-propanol to HYPDA-OLNa$_2$ was 96.7% of theory based on the starting amine. A gas chromatogram of the acidified, dried, and silylated product showed that HYPDA-OLNa$_2$ is the principal component of the hydrolysis mixture.

PROCEDURE 1

A 74.1 g portion (1 mole) of 1,3-propanediamine can be fed into 50 ml of water in a reaction zone. The resulting aqueous solution of the amine will become hot (reaching a temperature of about 60° C at it is formed). Said mixture can be cooled to 50° C and a premix of 204.6 g (3 moles) of 44% formaldehyde and 84 ml (2.1 moles) of HCN (which has been stabilized with 0.4 g of 85% H$_3$PO$_4$) having a temperature of 15° C can be added thereto over a period of 1½ hours. The temperature of the mixture in the reaction zone increases as the formaldehyde and HCN are added thereto. Said temperature can be allowed to reach a maximum of 70° C. Within a few minutes of the end of the premix feed, white crystals of the nitrile product will crystallize exothermally. The mixture from which the crystals precipitate (with the crystals therein) can be stirred for 2 hours while maintaining it at 60°–70° C; then the mixture can be cooled to 25° C, filtered, and the separated nitrile crystals can be washed with cold water. The washed nitrile can be dried in air or at 50° C. About 138 g of product (HYPDAN) corresponding to a conversion (one pass yield) of 85% will be obtained.

From the above examples and procedure, it is readily seen that in the preparation of HYPDAN, glycolonitrile is equivalent on a mole-for-mole basis to 1 mole of formaldehyde plus 1 mole of HCN.

PROCEDURE 2

The method of Example 5 can be used to prepare other alkali metal and alkaline earth metal hexahydropyrimidine-1,3-diacetates by replacing sodium hydroxide with the same number of equivalents of potassium hydroxide, lithium hydroxide, barium hydroxide, or calcium hydroxide, for example, in the saponification of HYPDAN.

PROCEDURE 3

The pH of the ammonia-free HYPDANa$_2$ solution prepared in Example 5 can be adjusted to pH 3.8 by adding concentrated hydrochloric HCl acid (ca. 37.5% HCl) thereto.

The resultant solution can be concentrated by evaporation to yield a slurry of the major part of the sodium chloride in a PDDA/CH$_2$O solution. The sodium chloride can be removed by filtration. Sodium chloride can be removed in this manner as many times as is practical by alternate concentrating and filtering. The final filtrate can be evaporated to near dryness and the residue recrystallized from hot water/methanol mixtures to yield the solid product on cooling. Said product can be filtered off, washed with methanol, recovered and dried. The solid is PDDA (containing a minor amount of sodium chloride).

PROCEDURE 4

PDDA can be precipitated from the pH 3.8 solution of Procedure 3 by the addition of large amounts of methanol (10 times the volume of PDDA solution) to the PDDA/formaldehyde/sodium chloride solution. The PDDA can be filtered off, washed with methanol/water mixtures, recovered, and dried.

PROCEDURE 5

The reaction of a solution of 190 g (1 mole) of PDDA with 80 g (2 moles) of sodium hydroxide can form a first solution of disodium 1,3-propanediamine-N,N'-diacetate. The addition of 68.2 g (1 mole) of 44% formaldehyde to said first solution can form a second solution of 246 g (1 mole) of HYPDANa$_2$.

PROCEDURE 6

Various hexahydropyrimidine-1,3-diacetates of the formula given below can be prepared using the general method of Procedure 5 by replacing sodium hydroxide with the same number of equivalents of another hydroxide:

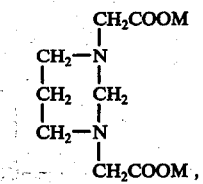

where M is an alkali metal ion, ½ an alkaline earth metal ion, or an ammonium ion of the formula

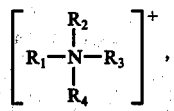

wherein $R_1$, $R_2$, $R_3$, and $R_4$ is each independently hydrogen, lower alkyl, or hydroxy lower alkyl.

PROCEDURE 7

HYPDANOL can be prepared from the 1,3-diamino-2-propanol/formaldehyde mixture (prepared according to the method of Example 11) by using the general method of Example 12 but replacing the glycolonitrile of Example 12 with an equivalent amount of formaldehyde and HCN.

PROCEDURE 8

HYPDANOL can be prepared directly from 1,3-diamino-2-propanol and a formaldehyde/HCN premix using the general method described in Procedure 1, supra, wherein 1,3-diamino-2-propanol is substituted for the 1,3-propanediamine of Procedure 1.

PROCEDURE 9

The method of Example 13 can be used to prepare other alkali metal and alkaline earth metal 5-hydroxyhexahydropyrimidine-1,3-diacetates by replacing sodium hydroxide with the same number of equivalents of potassium hydroxide, lithium hydroxide, barium hydroxide, or calcium hydroxide, or the like, in the saponification of HYPDANOL.

PROCEDURE 10

The method of Example 6 or 7 can be used to acidify HYPDA-OLNa$_2$ and to isolate 1,3-diamino-2-propanol-N,N'-diacetic acid (HYDROXY-PDDA) therefrom,

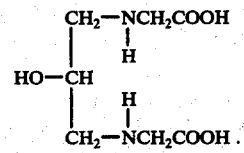

PROCEDURE 11

The method of Example 8 can be used to form HYDROXY-PDDA dihydrochloride,

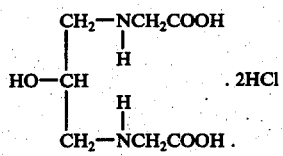

HYDROXY-PDDA can be prepared therefrom using the method of Example 8.

PROCEDURE 12

The method of Example 10 can be used to prepare HYDROXY-PDDA sulfate.

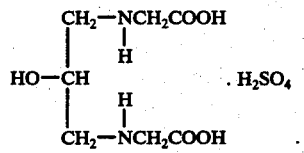

PROCEDURE 13

The reaction of a solution of 206 g (1 mole) of HYDROXY-PDDA with 40 g (1 mole) of sodium hydroxide can be used to prepare a solution of the monosodium hydrogen HYDROXY-PDDA. Various other monosalt hydrogen 1,3-diamino-2-propanol-N,N'-diacetates of the formula given below can be prepared by replacing the sodium hydroxide with the same number of equivalents of another hydroxide.

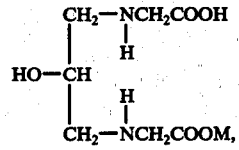

wherein M is an alkali metal ion, ½ and alkaline earth metal, or an ammonium ion of the formula

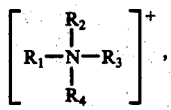

in which $R_1$, $R_2$, $R_3$, and $R_4$ is each independently hydrogen, lower alkyl, or hydroxy lower alkyl.

PROCEDURE 14

The reaction of a solution of 206 g (1 mole) of HYDROXY-PDDA with 80 g (2 moles) of sodium hydroxide can be used to prepare a solution of disodium HYDROXY-PDDA. The addition of 68.2 g (1 mole) of 44% formaldehyde will produce a solution of 262 g (1 mole) of HYPDA-OLNa$_2$ —

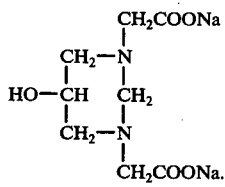

PROCEDURE 15

Various 1,3-diamino-2-propanol-N,N'-diacetates and various 5-hydroxy-hexahydropyrimidine-1,3-diacetates of the formulas given below can be prepared using the metod of Procedure 14 by replacing the sodium hydroxide with the same number of equivalents of another hydroxide:

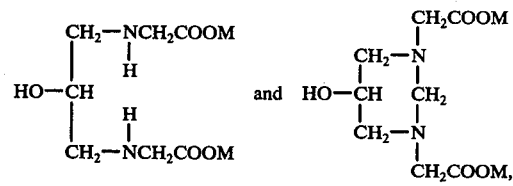

where M is as defined in Procedure 13.

PROCEDURE 16

This procedure illustrates a method which can be used to prepare

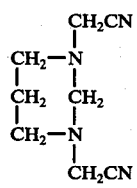

by the reaction represented by the equation

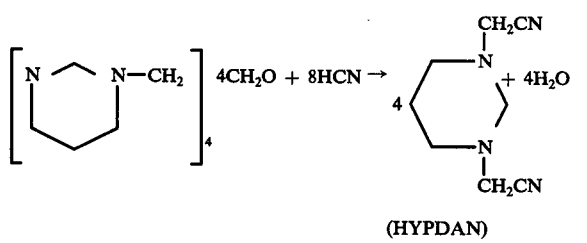

(HYPDAN)

wherein $$\left[ \begin{array}{c} N \frown N-CH_2 \\ \smile \end{array} \right]_4 ,$$

a tetramer of 1,3-propanediamine and formaldehyde is used as starting amine:

98.0 g (0.25 mole) of said tetramer of 1,3-propanediamine and CH$_2$O can be slurried in 125 ml of water. 42 ml (1.05 moles) of HCN can be fed in over 30 minutes from 25° to 55° C. The resulting mixture is held at 50°–55° C for 30 minutes until most of the amine dissolves. A premix of 68.2 g (1.0 mole) of 44% CH$_2$O and 42 ml (1.05 moles) of HCN stabilized with 0.2 g of 85% H$_3$PO$_4$ can be fed in over 30 minutes (65° C maximum temperature). White crystals of the nitrile will precipitate within a few minutes of the end of the feed. The slurry can be stirred for 2 hours at 50°–55° C, then cooled to 25° C, filtered, washed with water, and dried at 50° C. About 138 g (85% yield) of HYPDAN will be obtained.

PROCEDURE 17

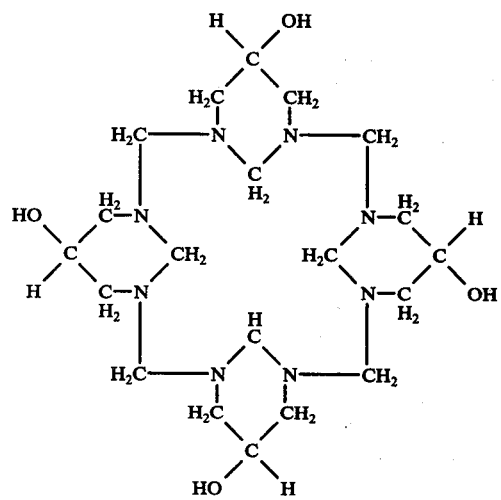

which elswhere in this specification, is referred to as

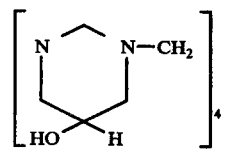

can be prepared by the general procedure of Krässig (Makromol. Chem., 1956,17, 77–130 (at 87–88)) wherein said general procedure is modified by replacing the 1,3-propanediamine of Krässig with an equal molar amount of 1,3-diamino-2-propanol.

PROCEDURE 18

The general method of Procedure 16 can be used to prepare HYPDANOL wherein said general method is modified by replacing the

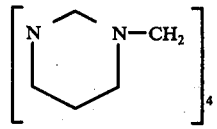

of Procedure 16 with

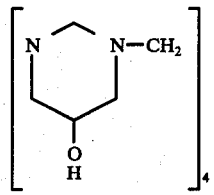

which can be prepared according to the method of Procedure 17.

As used herein, the term "ml" means milliliter or milliliters.

As used herein, the term "g" means gram or grams.

As used herein, the term "mole" has its generally accepted meaning, a mole being that quantity of a substance which contains the same number of molecules of the substances as there are atoms in 12 g of pure $^{12}C$.

As used herein, the term "percent (%)" means parts per hundred, and the term "parts" means parts by weight unless otherwise defined where used.

As used herein, the term "water soluble alcohol" means an alcohol (including a diol or a polyol) which is miscible or substantially miscible with water in all proportions or in substantial all proportions.

As used herein, the term "equivalent" as applied to alkali metal or alkaline earth metal hydroxide means that quantity of hydroxide which will provide 17.007g of hydroxide ions.

As used herein, the term "equivalent" as applied to an acidic ion exchange resin means that amount of the ion exchange resin which will provide 1.008 g of hydrogen ions.

A stoichiometric amount of sodium (or potassium) hydrogen carbonate based on PDDA dihydrochloride or HYDROXY-PDDA dihydrochloride is 2 moles of the sodium (or potassium) hydrogen carbonate per mole of such dihydrochloride.

A lower alkyl group is an alkyl group having about 1-7 carbon atoms, and a hydroxy lower alkyl group is a lower alkyl group in which one of the hydrogens has been replaced by a hydroxy (—OH) group.

As used herein:

"PDDA" means N,N'-dicarboxymethyl-1,3-propanediaminediacetic acid.

"HYDROXY-PDDA" means N,N'-dicarboxymethyl-2-hydroxy-1,3-propanediaminediacetic acid.

"HYPDANa$_2$" means disodium hexahydropyrimidine-1,3-diacetate.

"HYDROXY-HYPDANa$_2$" and "HYPDA-OLNa$_2$" means disodium 5-hydroxyhexahydropyrimidine-1,3-diacetate.

"HYPDAN" means hexahydropyrimidine-1,3-diacetonitrile.

"HYPDANOL" means 5-hydroxyhexahydropyrimidine-1,3-diacetonitrile.

"HYPDA-OLNa$_2$" means disodium 5-hydroxyhexahydropyrimidine-1,3-diacetate.

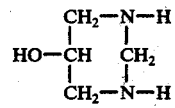

We claim:

1. A compound having the formula